United States Patent [19]
Concha

[11] Patent Number: 5,894,020
[45] Date of Patent: Apr. 13, 1999

[54] SOAP COMPOSITION CONTAINING ANTIFUNGAL AGENT

[76] Inventor: Jose Concha, 341 Prospect Rd., Springfield, Pa. 19064

[21] Appl. No.: 08/844,068

[22] Filed: Apr. 18, 1997

[51] Int. Cl.$^6$ ............................................. A61L 9/04
[52] U.S. Cl. .......................... 424/405; 252/106; 252/107; 252/108; 252/117; 252/122; 252/542; 252/545; 252/546; 252/547; 424/195.1; 514/919
[58] Field of Search ........................... 424/195.1, 405; 514/919; 252/542, 117, 546, 547, 545, 106, 107, 108, 122

[56] References Cited

U.S. PATENT DOCUMENTS

| | | | |
|---|---|---|---|
| 3,505,412 | 4/1970 | Klien | 260/631.5 |
| 4,477,361 | 10/1984 | Sperti et al. | 252/106 |
| 4,919,846 | 4/1990 | Nakama et al. | 252/542 |
| 5,096,709 | 3/1992 | VanderSloot | 424/195.1 |
| 5,385,733 | 1/1995 | Mankovitz | 424/195.1 |
| 5,449,517 | 9/1995 | Fitzjarrell | 424/195.1 |
| 5,455,033 | 10/1995 | Silverman | 424/195 |
| 5,468,473 | 11/1995 | Mullen | 424/66 |
| 5,472,684 | 12/1995 | Nabi | 424/49 |
| 5,529,784 | 6/1996 | DiPippo | 424/443 |
| 5,588,914 | 12/1996 | Cohen | 424/59 |

OTHER PUBLICATIONS

Australian Medicinal Plants, by Lassak & McCarthy pp. 95–97.

Primary Examiner—Terressa Mosley
Attorney, Agent, or Firm—LaMorte & Associates

[57] ABSTRACT

A compound and method for treating tinea pedis. An antifungal agent, such as *melaleuca alternifolia* extract oil, is added to the ingredients of soap in a concentration that is great enough to treat tinea pedis when the skin is washed with the soap. As a result, a person is effectively applying a preventative treatment of the antifungal agent each time that person baths with the soap. The duration of the treatment is regulated by selectively altering the size and/or amount of soap. Other ingredients can also be added to the soap to increase the effectiveness of the antifungal agent. Furthermore, fragrance can be added to the soap to mask any unpleasant odor that may be associated with the antifungal agent or the other active ingredients.

17 Claims, 1 Drawing Sheet

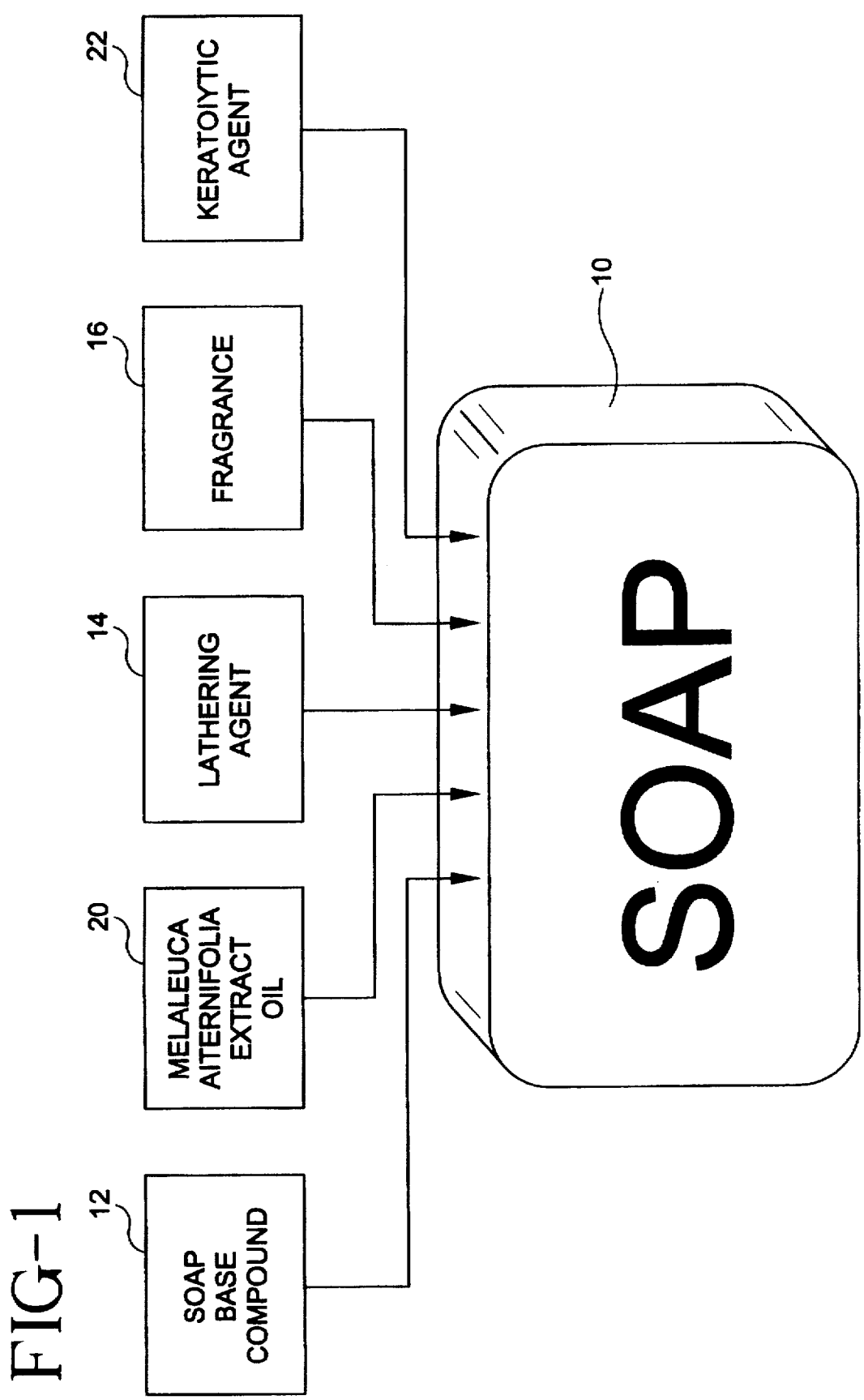

5,894,020

SOAP COMPOSITION CONTAINING ANTIFUNGAL AGENT

BACKGROUND OF THE INVENTION

1. Field of the Invention

In general, the present invention relates to soap, such as bars of soap, that are used for personal hygiene. More particularly, the present invention relates to bars of soap containing antimicrobial compounds.

2. Description of the Prior Art

Tines pedis, i.e. athlete's foot, is a common fungus infection that afflicts millions of people. Tines pedis is contagious and is caught when a person's skin comes into contact with a surface containing the fungus. If the skin conditions are proper, the fungus will grow and infect the surrounding skin.

The prior art is replete with pharmaceutical compositions that have be developed to treat tines pedis. Some of these prior art compounds require a prescription, while many others are commercially available over-the-counter to the general public. With either prescription treatments or over-the-counter treatments for tinea pedis, a person typically only uses the treatment for as long as symptoms exist. Prescription and over-the-shelf treatments are often expensive and a person quickly stops using the treatment as soon as the tinea pedis seems to be gone. The problem that then occurs is that the person temporarily cured of the tinea pedis reinfects himself/herself by bringing their feet back into contact with an infected surface. Tinea pedis lives in the shoes, socks, showers and bathrooms of those who have the fungus infection. After a person has successfully treated the fungus on their feet, they often reinfect their own feet by wearing infected shoes or walking on infected surfaces.

In order to prevent the reoccurrence of tinea pedis, a person must continue to medicate his/her own skin until the residual tinea pedis in the person's shoes and walking surfaces dies away. The only other option is the impractical step of replacing all footwear and sterilizing all walking surfaces. Due to the expense of many commercial antifungal treatments, prolonged use is not economical. Furthermore, many commercial antifungal treatments contain harsh ingredients that can cause skin irritation if used for prolonged periods of time. As a result, such commercial treatments can not be used as a long term preventative treatment against the reoccurrence of tinea pedis.

Additionally, commercial treatments often come in the form of powder or topical creams. In order for a person to apply such commercial treatments to the feet, the person must remove his/her socks and shoes. This adds to the inconvenience of treating the tinea pedis and further adds to the unlikelihood that people will apply preventative medicine to their feet after the initial tinea pedis infection has been cured.

A need therefore exists in the art for a treatment for tinea pedis that can be used for extended period of time without adverse effects. A need also exists for a method of applying the treatment to the feet that is not an inconvenience. These needs are provided for by the present invention as set forth in the below description and claims.

SUMMARY OF THE INVENTION

The present invention is a compound and method for treating tinea pedis. An antifungal agent, such as *melaleuca alternifolia* extract oil, is added to the ingredients of soap in a concentration that is great enough to treat tinea pedis when the skin is washed with the soap. As a result, a person is effectively applying a preventative treatment of the antifungal agent each time that person baths with the present invention soap. The person receiving treatment therefore does not have to apply any medications separately and the duration of the treatment can be regulated by selectively altering the size and/or amount of soap. Other ingredients can also be added to the soap to increase the effectiveness of the antifungal agent. Furthermore, fragrance can be added to the soap to mask any unpleasant odor that may be associated with the antifungal agent or the other active ingredients.

BRIEF DESCRIPTION OF THE DRAWINGS

For a better understanding of the present invention, reference is made to the following description of an exemplary embodiment thereof, considered in conjunction with the accompanying drawing, in which:

FIG. 1 schematic block diagram showing a bar of soap in accordance with the present invention and the preferred ingredients used to produce the bar of soap.

DETAILED DESCRIPTION OF THE INVENTION

Although the present invention composition can be manufactured in different forms, such as liquid soap and powdered soap, the present invention composition is particularly well suited for use in a solid bar of soap. As a result, by way of an example, the present invention composition will be described as configured as a solid bar of soap in order to set forth the best mode contemplated for the present invention.

Referring to FIG. 1 there is shown a bar of soap 10 in accordance with the present invention. The bar of soap 10 contains many of the same ingredients that are found in traditional bars of soap. Those traditional ingredients includes a soap base compound 12, which is typically a combination of a pot ash, a soda and a vegetable or animal fat. The prior art is replete with different combination of compounds that serve as a soap base. Most any such prior art composition can be adapted for use in the present invention. In the preferred embodiment, the fat used to create the soap base compound is a vegetable oil which lends itself better to mixing with the oil of the melaleuca alternifolia species of plant, as will later be explained.

Many modern bars of soap also include a lathering agent 14, such as tetrasodium EDTA, that help produce a thick, rich lather when the bar of soap 10 is agitated in the presence of water. In the present invention composition, the use of such a lathering agent 14 is preferred but is not required.

Traditional soap compositions also include fragrance 16. Although fragrance and does not add to the function of the soap, it add greatly to the aesthetics of the soap and its consumer appeal. As such, it should be understood that the bar of soap 10 can be made with any desired fragrance. *Melaleuca alternifolia* extract oil 20 is used in the preferred embodiment of the invention, as will later be explained. *Melaleuca alternifolia* extract oil has a pungent smell that is reminiscent of that of nutmeg. Such an aroma is not particularly pleasing for a soap. As such, the preferred embodiment contains a fragrance in a concentration great enough to mask the aroma of the *melaleuca alternifolia* extract oil 20 as perceived by a person's olfactory sense.

In the present invention composition, an extract oil 20 of the plant species *Melaleuca alternifolia* is added as the primary antimicrobial agent. The *melaleuca alternifolia* is a shrub-like tree that is indigenous to the swampy north costal regions of Australia. The British Pharmaceutical Codex of 1949 lists *melaleuca alternifolia* as Oleum melaleuca consisting of terpinenes, cymene, pinene, 1-trepinen-e-ol, cineole, sequiterpenes and sesquiterpene alcohols. Extract oil 20 of *melaleuca alternifolia* is an oil that is extracted using a steam distillation technique. One kilogram of foliage produces between 12 grams and 25 grams of extract oil after distillation. Various compositions containing the extract oil, commonly known as tea tree oil, have been used as a topical medication for over a century. Currently, there are United States patents that use compositions containing *melaleuca alternifolia* extract oil for the treatment of sunburn, genital herpes, gingivitis, and flea infestation. Patents showing compounds containing *melaleuca alternifolia* extract oil are also used as topical muscle relaxers and as antiperspirants.

In a solid bar of soap 10 as is shown, *melaleuca alternifolia* extract oil 20 can be added in concentrations between 0.5% and 15% by volume, while still maintaining a solid bar of soap. In lower concentrations, the *melaleuca alternifolia* extract oil 20 can be mixed into an existing soap base compound prior 12 to drying into a bar of soap. However, the *melaleuca alternifolia* extract oil 20 can also be combined with other plant oils in the soap base compound 12 itself prior to mixing with pot ash and soda. As a result, the *melaleuca alternifolia* extract oil is part of the fat that reacts with the pot ash and soda to create the soap base compound 12. In a liquid soap, *melaleuca alternifolia* extract oil 20 can be added to the composition in concentrations as high as 80% by volume. In the preferred embodiment, the *melaleuca alternifolia* extract oil 20 is contained in a solid bar of soap 10 at a concentration of approximately 2% by volume.

Tinea pedis is caused by each of four pathogenic organisms. These organisms include *epidermophyton floccosum*, *trichophyton rubrum*, *candida albians* and *trichophyton mentagrophytes*. *Melaleuca alternifolia* extract oil 20 has been found to be a highly effective fungicide against all four of these organisms in the concentrations above specified. In such concentrations, the *melaleuca alternifolia* extract oil 20 is non-toxic and virtually hypoallergenic, wherein skin reactions to the extract oil 20 are extremely rare even during prolonged use, i.e. over six consecutive months. *Melaleuca alternifolia* extract oil 20 has anti-histamine properties which help the extract oil prevent adverse reactions with the skin.

As a result, when the *melaleuca alternifolia* extract oil 20 is added to a soap base composition 12 and made into a bar of soap 10, the bar of soap 10 retains the antifungal properties of the extract oil 20. The bar of soap 10 therefore serves as the dispensing medium through which a person can apply maintenance dosages of antifungal treatment to afflicted skin to prevent a reinfection. A person therefore only has to wash his/her feet with the bar of soap 10 everyday in order to apply the *melaleuca alternifolia* extract oil 20 to the feet. The extract oil 20 cures any current infection of tinea pedis and prevents any reinfection of the feet from shoes or other infected surfaces. One bar of soap 10 should last a person several weeks if that soap is only used to wash the feet. The preventative dosages of the *melaleuca alternifolia* extract oil 20 therefore can be maintained for several weeks which should be long enough to eliminate the infecting agent from the shoes and floor surfaces. A person will know when to stop using the treatment when the bar of soap 10 dissolves away. The full course of treatment can therefore be regulated by selectively altering the size, volume and/or dissolvability of the bar of soap 10. By applying the antifungal agent through the bar of soap 10, the person with the tinea pedis need not rub on creams or sprinkle on powder. Rather, the administration of the antifungal agent occurs during the normal everyday activity of washing.

People often have calluses and other areas of thickened skin on the feet. Tinea pedis may reside deep within cracks of such areas or even under such areas. Since areas of thickened skin tend not to absorb topical ointments as readily as normal skin, a keratolytic agent 22 such as salicylic acid may be used to soften the thick areas of skin and improve the absorption of the *melaleuca alternifolia* extract oil 20.

It will be understood that the embodiments of the present invention described and illustrated herein are merely exemplary and a person skilled in the art can make many variations to the embodiment shown without departing from the scope of the present invention. It should also be understood that the various elements from different embodiment can be mixed together to create alternate embodiments that are not specifically described. All such variations, modifications and alternate embodiments are intended to be included within the scope of the present invention as defined by the appended claims.

What is claimed is:

1. A solid bar of soap for washing skin, comprising:
   a soap base compound;
   *melaleuca alternifolia* extract oil in a concentration of at least 0.5%;
   a keratolytic agent to promote absorption of said *melaleuca alternifolia* extract oil into the skin; and
   a fragrance in a concentration large enough to mask the aroma generated by the *melaleuca alternifolia* extract oil.

2. The soap according to claim 1, wherein said concentration of *melaleuca alternifolia* extract oil is between 0.5% and 15%.

3. The soap according to claim 1, wherein said concentration of *melaleuca alternifolia* extract oil is approximately 2%.

4. The soap according to claim 1, further including a lathering agent.

5. The soap according to claim 1, wherein said keratolytic agent includes salicylic acid.

6. The soap according to claim 1, wherein said soap base compound includes result compounds from the reactions between a pot ash, a soda and a fat.

7. The soap according to claim 6, wherein said fat is a plant oil.

8. The soap according to claim 7, wherein said plant oil contains *melaleuca alternifolia* extract oil.

9. A soap composition for use on the skin, comprising:
   a pot ash;
   a soda;
   a fat;
   an antifungal agent; and
   a keratolytic agent to soften the skin and promote absorption of said antifungal agent into the skin.

10. The composition according to claim 9, further including a fragrance.

11. The composition according to claim 9, wherein said keratolytic agent includes salicylic acid.

12. The composition according to claim 9, wherein said antifungal agent includes *melaleuca alternifolia* extract oil.

13. The composition according to claim 9, wherein said fat is a plant oil.

14. The composition according to claim 13, wherein said plant oil includes *melaleuca alternifolia* extract oil.

15. The composition according to claim 9, wherein said composition is a liquid.

16. The composition according to claim 9, wherein said composition is configured as a solid bar of soap.

17. The composition according to claim 9, further including a lathering agent.

* * * * *